US006312666B1

(12) United States Patent
Oxman et al.

(10) Patent No.: US 6,312,666 B1
(45) Date of Patent: *Nov. 6, 2001

(54) METHODS OF WHITENING TEETH

(75) Inventors: Joel D. Oxman, St. Louis Park; Matt C. Trom, Cottage Grove, both of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/190,541

(22) Filed: Nov. 12, 1998

(51) Int. Cl.$^7$ ............................. A61K 7/16; A61K 7/20; A61K 6/00

(52) U.S. Cl. ................................ 424/49; 424/53; 433/215

(58) Field of Search ........................ 424/49–88; 433/215

(56) References Cited

U.S. PATENT DOCUMENTS

| | | | |
|---|---|---|---|
| 3,639,574 | * 2/1972 | Schmolka | 424/78 |
| 3,652,420 | 3/1972 | Hill . | |
| 4,011,309 | 3/1977 | Lutz . | |
| 4,100,271 | * 7/1978 | Krezanoski | 424/78 |
| 4,130,501 | * 12/1978 | Lutz et al. | 252/186 |
| 4,188,373 | * 2/1980 | Krezanoski | 424/78 |
| 4,474,751 | * 10/1984 | Haslam et al. | 424/78 |
| 4,474,752 | 10/1984 | Haslam et al. | 424/78 |
| 4,537,778 | * 8/1985 | Clipper et al. | 424/53 |
| 4,696,757 | * 9/1987 | Blank et al. | 424/53 |
| 4,719,149 | 1/1988 | Aasen et al. . | |
| 4,774,093 | * 9/1988 | Provenchee et al. | 424/483 |
| 4,795,527 | 1/1989 | Cohen . | |
| 4,839,156 | * 6/1989 | Ng et al. | 424/53 |
| 4,861,760 | * 8/1989 | Mazuel et al. | 514/54 |
| 4,888,168 | * 12/1989 | Potts et al. | 424/78 |
| 4,921,626 | 5/1990 | Rhodenbaugh . | |
| 4,980,152 | * 12/1990 | Frazier | 424/52 |
| 5,000,955 | * 3/1991 | Gould et al. | 424/409 |
| 5,059,417 | 10/1991 | Williams et al. . | |
| 5,061,183 | 10/1991 | Nicholson . | |
| 5,071,637 | 12/1991 | Pellico . | |
| 5,071,644 | * 12/1991 | Viegas et al. | 514/771.7 |
| 5,073,363 | 12/1991 | Pellico . | |
| 5,077,033 | * 12/1991 | Viegas et al. | 514/663 |
| 5,098,303 | 3/1992 | Fischer | 433/215 |

(List continued on next page.)

FOREIGN PATENT DOCUMENTS

| | | |
|---|---|---|
| 0 102 200 A2 | 3/1984 | (EP) . |
| 288420 | * 10/1988 | (EP) . |
| 325 267 | 7/1989 | (EP) . |
| 535816 | * 4/1993 | (EP) . |
| 545 594 | 6/1993 | (EP) . |
| 612 512 | 8/1994 | (EP) . |
| 0 758 544 A2 | 2/1997 | (EP) . |
| 1 571 832 | 7/1980 | (GB) ........................... A61K/9/06 |
| 2 170 406 | 8/1986 | (GB) ........................... A61K/7/18 |
| 59 128330 A | 7/1984 | (JP) . |
| WO 86/00813 | 2/1986 | (WO) ......................... A61K/47/00 |
| WO 91/14650 | 10/1991 | (WO) ......................... C01B/15/00 |
| WO 96/02276 | 2/1996 | (WO) ......................... A61K/47/38 |
| WO 96/02577 | 2/1996 | (WO) ......................... C08B/15/00 |
| WO 96/06134 | 2/1996 | (WO) ......................... C08L/33/24 |
| WO 96/25457 | 8/1996 | (WO) ......................... C08K/9/12 |
| WO 96/28056 | 9/1996 | (WO) ......................... A43B/7/28 |
| WO 97/00275 | 1/1997 | (WO) . |
| 9711675 | * 4/1997 | (WO) . |
| WO 97/11675 | 4/1997 | (WO) ......................... A61K/7/20 |
| 9830494 | * 7/1998 | (WO) . |

OTHER PUBLICATIONS

Dentistry Today Buyers Guide To Whitening Systems 5 pages Syringe Delivery of Gellod Peroxide Tooth Whitener By Disco Dental Producs American Dental Products Den–Mat Interdent Harbor Dental Bleach OMNI Products Ultradent etc, Dec. 1997.*
BASF Wyandotte U.S. 3639574 Wong, Oct. 1972.*
Colgate Palmolive U.S. 5814304, Sep. 1998.*
colgate Palmolive U.S. 5766574 Christina Beck, Jun. 1998.*
Marion Cabs/Frazier et al U.S. 4980152, Dec. 1990.*
Blank/American 120MG U.S. 4696757, Sep. 1987.*
Pellico/Laclede U.S. 5718886, Feb. 1998.*
Pellico/Laclede U.S. 5631000, May 1997.*
Den–Mat Corporation, "The Innovative Company Behind *Rembrandt Products*, " product information sheets [on–line]. Den–Mat Corporation, 1998–1999 [retrieved on Mar. 13, 2000]. Retrieved from the Internet: <URL:http://www.rembrandt.com/denmat/about.htm> 14 pgs.
Den–Mat product information sheets [on–line]. Den–Mat Corporation, 1998–1999 [retrieved on Mar. 13, 2000]. Retrieved from the Internet: <URL:http//www.denmat.com /main/htm> 10 pgs.
Discuss Dental product information sheets for Professional Whitening Products [on–line]. Discuss Dental [retrieved on Mar. 13, 2000], Retrieved frome he Internet: <URL:http://www.discusdental.com/> 13 pgs.
Ultradent Online Materials and Procedures Manual [on–line]. Ultradent Products, Inc., 1999 [retrieved on Mar. 13, 2000]. Retrieved from the Internet: <URL:http://www.ultradent.com/> 20 pgs.
"Surfactants, Pluronic & Tetronic," BASF Product Information Brochure, Mount Olive, New Jersey, 40 pages (1999).
Haywood et al., "Nightguard Vital Bleaching," *Quintessence International*, vol. 20, No. 3, pp. 173–176 (1989).
BASF Product Literature, "BASF Performance Chemicals Pluronic® & Tetronic® Surfactants," BASF Corporation (1996).

*Primary Examiner*—Shep K. Rose

(57) ABSTRACT

Dental whitening compositions are provided that have the capability of undergoing an increase in viscosity in response to an increase in temperature. In a preferred embodiment, the compositions also have the ability to reverse their viscosity in response to a decrease in temperature.

20 Claims, 1 Drawing Sheet

U.S. PATENT DOCUMENTS

| | | | | |
|---|---|---|---|---|
| 5,122,365 | * | 6/1992 | Murayama | 424/49 |
| 5,124,151 | * | 6/1992 | Viegas et al. | 424/422 |
| 5,171,564 | * | 12/1992 | Nathoo et al. | 424/53 |
| 5,234,342 | | 8/1993 | Fischer | 433/215 |
| 5,252,318 | | 10/1993 | Joshi et al. | 424/78.04 |
| 5,256,065 | | 10/1993 | Nicholson . | |
| 5,256,396 | * | 10/1993 | Piechota | 424/49 |
| 5,300,295 | * | 4/1994 | Viegas et al. | 424/427 |
| 5,340,613 | * | 8/1994 | Hanzauk et al. | 427/412.5 |
| 5,376,006 | | 12/1994 | Fischer | 433/215 |
| 5,376,693 | * | 12/1994 | Viegas et al. | 523/106 |
| 5,376,695 | * | 12/1994 | Viegas et al. | 523/106 |
| 5,378,542 | * | 1/1995 | Hanzauk et al. | 428/483 |
| 5,401,495 | * | 3/1995 | Murayama | 424/49 |
| 5,409,630 | | 4/1995 | Lysy et al. . | |
| 5,409,631 | | 4/1995 | Fischer | 252/168.25 |
| 5,441,732 | | 8/1995 | Hoeg et al. | 424/78.04 |
| 5,492,937 | * | 2/1996 | Bogentoft et al. | 514/781 |
| 5,575,652 | * | 11/1996 | Gaffar et al. | 433/173 |
| 5,631,000 | * | 5/1997 | Pellico et al. | 424/53 |
| 5,718,886 | * | 2/1998 | Pellico | 424/53 |
| 5,725,843 | | 3/1998 | Fischer | 424/49 |
| 5,746,598 | | 5/1998 | Fischer | 433/216 |
| 5,766,012 | | 6/1998 | Rosenbaum et al. . | |
| 5,766,574 | * | 6/1998 | Christina-Beck et al. | 424/53 |
| 5,770,105 | | 6/1998 | Fischer | 252/186.25 |
| 5,814,304 | * | 9/1998 | Wong et al. | 424/53 |
| 5,819,988 | * | 10/1998 | Sawhney et al. | 222/137 |
| 5,846,570 | | 12/1998 | Barrow et al. . | |
| 5,847,023 | | 12/1998 | Viegas et al. . | |
| 5,851,514 | * | 12/1998 | Hassan et al. | 424/53 |
| 5,861,148 | | 1/1999 | Smith . | |
| 5,902,568 | * | 5/1999 | Ryles et al. | 424/53 |
| 5,928,628 | * | 7/1999 | Pellico | 424/49 |
| 6,116,900 | * | 9/2000 | Ostler | 433/89 |

* cited by examiner

METHODS OF WHITENING TEETH

FIELD OF THE INVENTION

This invention relates to dental whitening or brightening compositions having viscosities capable of responding to a change in temperature. The invention also relates to methods of whitening or brightening teeth surfaces using the composition, particularly methods of whitening or brightening teeth by dispensing the composition into a dental tray or directly onto tooth surfaces and keeping it in the mouth for some period of time.

BACKGROUND

Home teeth whitening systems have been available since the late 1980's, acquired either through a dental professional or over-the-counter. Prior to these systems, persons desiring whiter or brighter teeth were subjected to various heat or light activated systems provided by their dental practitioner in the dental chair. Typically, these practices involved the dental practitioner applying a hydrogen peroxide solution on the teeth, protecting the sensitive soft tissues with a ligated rubber dam, and applying heat to the applied solution to effectuate oxidation. Such oxidation removed discoloration from the tooth surfaces.

With the greater consumer demand for cosmetically enhancing products, aesthetic dentistry has correspondingly grown. The demand for these products also created interest in products which could be administered at a more convenient time and place, and/or with less equipment. Thus, numerous products have since been developed which provide a person with the means to treat and whiten his or her teeth in the privacy and convenience of the home.

Generally, to begin the whitening process, a user is provided with a dental tray, either by a dental practitioner or as part of a purchased dental whitening kit. The tray is intended to retain the whitening composition at the desired location(s) and maintain contact between the tooth surface and the whitening composition. When the treatment involves a dental practitioner, the dental tray is typically custom fitted to the user's personal denition. Some dental practitioners may choose to have selectively enlarged tooth-treating compartments or reservoirs fabricated within the dental tray which are adapted to receive a sufficient amount of tooth whitening composition. The purpose for having such reservoirs is to provide more whitening composition and to ensure, if desired, long-lasting exposure of the teeth to the whitening agent. The dental tray loaded with whitening composition is typically worn by the patient for some extended period of time (e.g. 30 minutes to 8 hours), depending on the degree of discoloration the user desires to remove. This treatment is repeated over a sufficient period of time to effect the tooth whitening and bleaching process.

Whitening compositions are generally formulated with thickening rheological modifiers such as carboxypolymethylene, cellulosic polymers, or fumed silicas in order for the compositions to be provided as a thickened composition. For example, Pellico, U.S. Pat. No. 5,361,000 is directed to dental whitening compositions thickened with glycerin and carboxypolymethylene. Pellico, U.S. Pat. No. 5,718,886 discloses a stabilized anhydrous dental whitening composition utilizing Xanthum gum as a thickening agent.

During the intraoral application of a tray and whitening composition, a system can increase from ambient temperature of about 22–25° C., to about 37° C. As a result of this temperature rise, the whitening composition may have a tendency to decrease in viscosity and become more flowable. In addition, the composition may also become diluted from saliva moving in and out of the tray, resulting in dilution of the composition. This thinning and viscosity decrease creates a tendency for the composition and thus the whitening agent, to flow out of the tray, resulting in a reduced amount of whitening composition available for treatment at the target location for the desired length of time.

To overcome the effect of temperature and salivation, a series of patents by Fischer, namely U.S. Pat. Nos. 5,098,303; 5,234,342; 5,376,006; 5,409,631; 5,770,105; 5,725,843; and 5,746,598 disclose teeth whitening compositions characterized with high viscosity and stickiness to minimize dilution from saliva and prolong the period of time the whitening agent is in contact with the teeth surfaces. These patents describe the use of high concentrations of carboxypolymethylene to provide the high viscosity characteristic of the whitening composition as it is stored in its container.

SUMMARY OF THE INVENTION

The invention provides a dental whitening composition whose viscosity is responsive to temperature changes, wherein the viscosity increases with an increase in temperature. These compositions also preferably have the ability to reverse their viscosity upon the lowering of temperature. The compositions of the invention comprise a whitening agent and a thermally responsive modifier.

Compositions of the invention work very well in the oral environment where temperature is generally higher than ambient or the pre-treatment temperature of a composition. This differential in temperature thickens the composition and thus provides a thickened, semi-solid or gel-like composition in the oral environment.

A preferred method of use of the invention comprises dispensing the composition into a dental tray that is subsequently placed into a user's mouth. Upon exposure of the composition to the oral temperature, the composition thickens to a semi-solid or gel-like state. Alternatively, the composition can be dispensed into a pre-warmed tray such that the composition thickens upon its contact with the tray.

DESCRIPTION OF THE INVENTION

Figure 1:
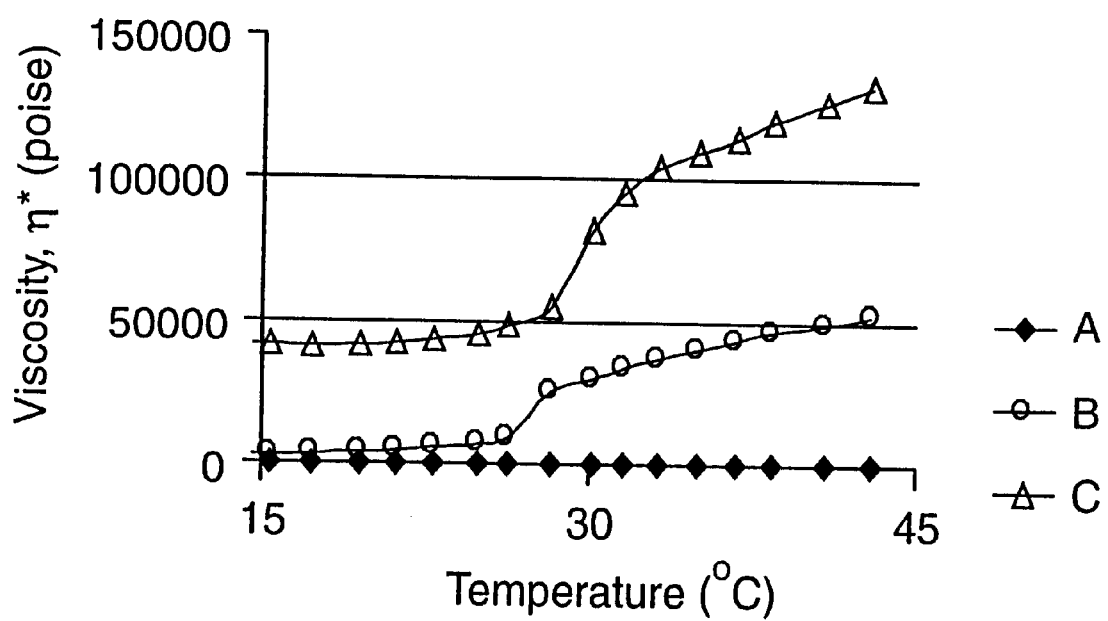
FIG. 1 is a graphic illustration of the viscosity versus temperature data as described in Example 3.

This invention overcomes the shortcomings of previous dental whitening compositions that experience a decrease in viscosity due to the increase in temperature from the intraoral environment. This is accomplished by providing dental whitening compositions that exhibit an increase in viscosity in response to an increase in temperature. As a separate advantage, compositions and methods of the present invention provide easy delivery of tooth whitening compositions, especially with those compositions that are initially a low viscosity liquid at its pre-treatment temperature. These compositions can be dispensed from delivery devices that have small orifices, require less force to dispense and become thicker or more viscous only upon being exposed to the temperature of the oral environment.

Compositions of this invention are particularly suitable for use in the intraoral environment where a composition having a pre-treatment temperature at or lower than ambient (room temperature) is applied to a user's tooth surfaces that is near or at oral temperature of about 30° C.–39° C. For certain dental applications, it is preferred that the composition be thermally reversible. In that application, the composition not only has the ability to increase its viscosity at an elevated intra-oral temperature, but also reverses or decreases its viscosity upon a decrease in temperature.

The capacity of the dental composition to thicken at human body temperatures is a critical feature of the invention, for it is in this property that many of the disadvantages of previous approaches are overcome. The dissipative characteristic of liquid solutions is avoided since the compositions herein experience thickening at the site of treatment. Moreover, the problems of formulation, handling, delivery and application of viscous compositions are overcome since the present compositions may be free-flowing liquids prior to treatment.

A "semi-solid," as used herein, is a material whose physical state is between a liquid and solid state, pure or mixed solvent or solution entrained within a network, and can be alternatively be considered as a gel. By "pure or mixed solvent and/or solution," as stated herein, it is recognized that a mixture of solvents may be absorbed by the network. Additionally, the solvent may include salts or other additives so as to form a solution, which may also be absorbed or entrained within the network.

"Thickening" as used herein, is where a composition undergoes a substantial increase in the viscosity of the composition. The degree of thickening is dependent on the initial viscosity of the composition.

In a preferred embodiment of the invention, the initial viscosity of the composition may be low enough such that the composition is in a liquid state. Subsequently, upon exposure to a temperature of about near or at body temperature, the viscosity increases to result in a thickened composition. A viscosity increase in the range of about 10- to about 100-fold can be experienced when the initial viscosity is low enough such that the composition is a liquid. Thus, for example, a composition in a liquid state may have a viscosity of about 0 to about 7000 poise. In response to an increase in temperature, the viscosity of the composition can increase to at least about 10,000 poise. Upon the lowering of the temperature, the composition preferably has the ability to reverse its viscosity and return to flow properties of a liquid.

Yet another preferred embodiment of the invention is when the initial viscosity of the composition is at a level at which the composition is in a semi-solid or gelatinous state at pre-treatment temperature, and upon exposure to a higher treatment temperature, the composition transforms into an "ultra-thick" or "ultra-gel" composition or one with a substantially higher viscosity and very low flow characteristics. These compositions typically have an initial viscosity of no less than about 7000 poise, which then thicken about 2- to about 5-fold.

The pre-treatment temperature is the temperature at which the composition is subjected to prior to application or treatment. The range for the pretreatment temperature can be about 5° C. to about 29° C., although there may be certain instances where the temperature may be outside this range. Having a pre-treatment temperature at about 2° C. to 25° C. allows the composition to be easily stored at ambient or room temperature. Alternatively, the compositions of the invention can also be advantageously stored at lower, refrigeration pre-treatment temperatures of about 5° C. to about 10° C. to provide improved stability and shelf life.

The treatment temperature is the temperature at which the composition is exposed to during intraoral application. This can be at or near body temperature, or about 30° C. to about 39° C.

In accordance with the invention, the dental composition consists of a water-miscible, physiologically compatible medium which is a liquid or gel at ambient temperature below about 30° C. and experiences thickening at oral temperatures above about 30° C. It has been found that a composition having a thickening transition temperature in the range of from about 25° C. to about 40° C. is useful in the practice of the present invention. Preferably, the thickening occurs in a temperature range of from about 25° C. to about 39° C., and more preferably from about 30° to about 35° C.

Compositions of this invention are comprised of a solvent, a whitening agent and a thermally responsive viscosity modifier that provides the desired viscosity increase at the desired elevated temperature range. Optionally, other adjuvants may be added to the composition. Preferably, the composition of this invention should be physiologically compatible so that no adverse reaction occurs if the tooth whitening composition comes in contact with human tissue or fluids. The solvent, whitening agent, and thermally responsive viscosity modifier may be contained in one mixture or contained separately in a multiple-part system. In a multiple-part system, the whitening agent may be kept physically separate from the viscosity modifier, to be admixed just prior to treatment.

As used herein, a "thermally responsive viscosity modifier" is one or more polymeric substances that provides the composition or polymeric system the capability of substantially increasing its viscosity in response to an increase in temperature. Suitable polymeric substances useful as thermally responsive viscosity modifiers include polyoxyalkylene polymers, particularly the polymeric surfactants available under the tradename PLURONIC. This class of polymers is available commercially from BASF Wyandotte Corporation. Other polyoxyalkylene polymers may also be useful as a thermally-responsive composition material.

A preferred dental composition in accordance with this invention comprises in aqueous solution of a selected polyoxyethylene-polyoxypropylene block copolymer. A composition comprising polyoxyethylene-polyoxypropylene block copolymers in which the number of polyoxyethylene units is at least about 50% of the number of units in the total molecule, and the block copolymer having an average molecular weight of from about 1100 to about 15,500 has been found to be particularly useful. It is more preferable that a composition comprises about 70% polyoxyethylene units of the total number of monomeric units in the copolymer and the copolymer has an average molecular weight of about 11,500. PLURONIC F-127 is a material that meets these criteria.

The PLURONIC polymers are closely related block copolymer that may be generically classified as polyoxypropylene-polyoxyethylene condensates that terminate in primary hydroxyl groups. These polymers are formed by the condensation of propylene oxide into a propylene glycol nucleus followed by the condensation of ethylene oxide onto both ends of the polyoxypropylene base. The polyoxyethylene hydrophilic groups on the ends of the base pre-polymer are controlled in length to constitute from about 10% to about 80% by weight of the final polymer.

The PLURONIC polymer series of products may be represented empirically by the formula: $HO(C_2H_4O)_a(C_3H_6O)_b(C_2H_4O)_cH$ where a and c are statistically equal.

The concentration of the block copolymers is an important parameter and can be formulated in such a manner corresponding to the other components' concentrations. By adjusting the concentration of the copolymer to accommodate other solutes present in the composition, any desired liquid to semi-solid transition temperature in the critical range of above ambient temperature and below body temperature can be achieved. Thus, the principal consideration is the selection of a concentration which, in conjunction with all of the constituents of the composition, will provide a liquid to semi-solid transition or alternatively, a gel to "ultra-gel" transition temperature in the required range.

It has been found that a useful block copolymer concentration is from about 5% to about 40% by weight (wt. %) of the composition, preferably from about 15 wt. % to about 26 wt. % of the composition. Excellent results have been obtained using aqueous solutions having from about 17 wt. % to about 26 wt. % of PLURONIC F-127.

Another known system which is liquid at room temperature, but forms a semi-solid when warmed to about body temperature is formed from tetrafunctional block polymers of polyoxyethylene and polyoxypropylene condensed with ethylenediamine, commercially available under the tradename TETRONIC polymer (BASF Wyandotte Corp.). These compositions are formed from approximately 10% to 50% by weight of the polymer in an aqueous medium. See, for example, U.S. Pat. No. 5,252,318 which is incorporated by reference herein.

Particularly preferred polymers for compositions of the invention are the PLURONIC F-127 and F-108 and the class of TETRONIC polymers. These viscosity modifiers are block copolymers of ethylene oxide and propylene oxide. Thickening tendencies of block copolymers increase as ethylene oxide content and total molecular weight increase. Thermally responsive block copolymers have been disclosed in U.S. Pat. Nos. 4,474,751; 4,474,752; 5,441,732; and 5,252,318, as well as the Product Catalog, "BASF Performance Chemicals," all the teachings of which are incorporated by reference herein. These block copolymers offer extremely low toxicity and a high degree of mildness for applications involving human contact.

A preferred solvent for the composition of this invention is water. The concentration of water in the composition can be in the range of from about 30 wt. % to about 90 wt. % of the composition, and is preferably from about 50 wt. % to about 80 wt. %. More preferably, water can exist in the range of about 50 wt. % to about 75 wt. % of the composition. The water used in forming the aqueous solution is preferably purified, as by distillation, filtration, ion-exchange or the like.

Other solvents may be used, including anhydrous solutions comprising a polyol component such as propylene glycol or polyethylene glycol. Propylene glycol may be present in the composition in an amount from about 10 wt. % to about 55 wt. % of the composition. Polyethylene glycol may be used in the practice of this invention, having a, molecular weight from about 400 to about 1500 and may be in an amount from about 10 wt. % to about 50 wt. % of the composition. Glycerin may also be used as a constituent of the composition.

The whitening agent used in the present invention may be any material that has the effect of whitening teeth. Whitening agents are preferably selected from hydrogen peroxide and its urea complex: carbamide peroxide $(CO(NH_2)_2H_2O_2)$. These whitening agents are also known by alternative names, including, urea hydrogen peroxide, hydrogen peroxide carbamide, or perhydrol-urea. Alternatively, sodium hypochlorite may be suitable for use as the whitening agent. The concentration of a whitening agent in the composition can vary depending upon its reactivity. With carbamide peroxide, for example, the currently preferred concentration range is from about 3% to about 40%, with a range from about 4% to about 21% being most preferred. In the case of hydrogen peroxide, which is more reactive than carbamide peroxide, the currently preferred concentration range is from about 2% to about 10%.

Other adjuvants can be added to the composition for certain purposes. For example, a preferred embodiment of the invention can contain fluoride, a desirable additive in oral compositions. Additives may also be included in the composition to promote the stability of the formulation. Anti-microbial agents, antifungal agents, and preservatives may be added to the composition to improve its shelf-life. Adhesive modifiers, which reduce or increase the stickiness of the composition may also be included in the formulation. The compositions may further include other adjuvants such as fillers, dyes, cariostatic agents, flavorings, sweeteners, medicaments and sodium bicarbonate.

Various methods can be employed in using the composition of this invention. One method of use of these whitening compositions entails application of the composition to the tooth structure directly from the composition's container or dispenser such as a bottle, syringe, or tube. Alternatively, the whitening composition can be applied by using a brush to paint it onto the tooth surface. The composition is kept on the user's tooth surface(s) for a desired time period to effectuate whitening. The length of time the composition is in contact with the tooth surface(s) would depend on the amount of discoloration the user prefers to remove.

In a preferred method, the whitening composition is loaded into a dental tray. Such dental trays can be custom fitted to a user's denition and be made with or without reservoirs. A preferred reservoir is described in U.S. patent application No. 53911USA1A, filed on Aug. 13, 1998, entitled Medication Delivery Tray, assigned to the assignee of the present invention, the disclosure of which is incorporated herein by reference. Dental trays can be made from varying thicknesses and softness of pliable thermo-formable plastic materials. Typically, these materials are 0.02–0.08 inches thick. After dispensing or loading the whitening composition into the dental tray, the user then places the loaded tray into the mouth and initiates thickening of the composition. The thickening occurs when the composition is exposed to the elevated treatment temperature of the oral environment. The tray is retained in the mouth to effectuate whitening of the tooth surface(s) for a sufficient period of time to remove discoloration.

An alternative method of use incorporates a pre-warmed dental tray into which the composition is loaded. Upon contact of the composition having a pre-treatment temperature, with the tray having a higher temperature, the composition experiences thickening. This method provides easy handling of a loaded tray into a user's mouth, with minimal fear of the composition moving to an undesired section of the tray or having the composition flow out of the tray.

Where the compositions are thermally reversible, the composition can be readily removed from the denition or tray by cooling the material below the liquid to semi-solid transition temperature, thus reversing the thickening effect. This can be accomplished with cool water or other physiologically compatible liquid. Alternatively, the concentrations of the components in the whitening composition may be adjusted and diluted by adding water or other liquid solution in the oral cavity. By adjusting the concentrations of the components, the transition temperature is correspondingly adjusted, and thus provides the user the ability to remove the composition even with warm solutions. Water or other liquid solutions may be administered through a rinsing cup, squirt bottle, a liquid dispensing dental tool, or any other liquid dispensing device that can provide solution to the oral environment. Preferably, administrating of cool or cold water onto the composition can provide a significant decrease in viscosity. Alternatively, the composition may be brushed, wiped, or blown off.

These and other aspects of the invention are illustrated by the following examples which should not be viewed as limiting in scope. Unless otherwise indicated, all molecular weights are number average molecular weights and all ratios, parts and percentages are by weight.

EXAMPLES

Preparation of Stock Solution 1

An aqueous stock solution containing approximately 15% hydrogen peroxide($H_2O_2$) was prepared by transferring 5 grams of a 30% $H_2O_2$ (J. T. Baker) and 5 grams of distilled water to a glass vial. The stock solution was mixed thoroughly.

Preparation of Stock Solution 2

An aqueous stock solution containing approximately 20% urea hydrogen peroxide (carbamide peroxide) was prepared by transferring 4 grams of 97% urea hydrogen hydrogen peroxide (Sigma) and 16 grams of distilled water to a glass vial. The stock solution was mixed thoroughly. (The hydrogen peroxide content of the urea hydrogen peroxide was about 35%). Stock solution contained about 7% $H_2O_2$.

Example 1

A thermally-reversible hydrogen peroxide composition was prepared by transferring the ingredients below to a glass vial and mixing thoroughly until a colorless and transparent liquid solution was obtained.

| Stock Solution 1 | 1.60 grams |
|---|---|
| PLURONIC F127 (BASF) | 0.40 grams |
| | 2.00 grams |

The above solution contained approximately 12% hydrogen peroxide, 68% water and 20% PLURONIC F127. The glass vial containing the liquid peroxide solution was warmed to body temperature by holding the vial in a human hand. Following about one to two minutes, the liquid was transformed into a colorless, transparent composition that did not flow upon inverting the vial. The vial was allowed to cool to room temperature wherein the composition was transformed back to the low viscosity state. This cycle was repeated several times with the same outcome.

The liquid and semi-solid (gel) states were both semi-quantitatively evaluatedfor hydrogen peroxide utilizing hydrogen peroxide analysis strips. The analysis utilized "EM Quant Peroxide Test Strips" (EM Science Gibbstown, N.J., Catalog No. 10011-1). The compositions were evaluated according to the manufacturer's directions.

Results of the tests indicated that both the liquid and semi-solid states contained significant amounts of available peroxide.

The same sample was re-evaluated 2 months later and found to still exhibit thermally-reversible characteristics and comparable hydrogen peroxide levels based oil the semi-quantitative analysis.

Example 2

A thermally reversible composition containing urea hydrogen peroxide was prepared by transferring the ingredients below to a glass vial and mixing thoroughly until a colorless and transparent liquid solution was obtained.

| Stock Solution 2 | 4.00 grams |
|---|---|
| PLURONIC F127 (BASF) | 1.00 grams |
| | 5.00 grams |

The above solution contained approximately 16% urea hydrogen peroxide (or about 5.6% hydrogen peroxide), 64% water and 20% PLURONIC F127. The glass vial containing the liquid peroxide solution was warmed to body temperature by holding the vial in a human hand. After about 1 minute, the liquid transformed to a colorless, transparent composition that did not flow upon inverting the vial. The vial was allowed to cool to room temperature wherein the semi-solid composition was transformed back to the low viscosity state. This cycle was repeated several time with the same outcome.

The liquid and semi-solid states were both semi-quantitatively evaluated or hydrogen peroxide utilizing hydrogen peroxide analysis strips, EM Quant Peroxide Test Strips (EM Science; Gibbstown, N.J., Catalog No. 10011-1), according to the manufacturer's directions. Both the liquid and semi-solid states indicated the presence of significant amounts of available peroxide.

The same sample was re-evaluated 9 days later and found to still exhibit thermally-reversible characteristics and comparable hydrogen peroxide levels based on the semi-quantitative analysis.

Table 1 summarizes the results of the two previous examples. The "+" indicates a increase in the viscosity. The "−" indicates a decrease in the viscosity. The presence of hydrogen peroxide as indicated in the table are the results obtained from the semi-quantitative test using the EM Quant Peroxide Test Strips and test method.

TABLE 1

| | % Peroxide | 35° C. viscosity | 35° C. viscosity @ 9 days | 25° C. viscosity | 25° C. viscosity @ 9 days | $H_2O_2$ Present | $H_2O_2$ Present @ 9 days |
|---|---|---|---|---|---|---|---|
| Example 1 | 12 | + | + | − | − | Yes | Yes |
| Example 2 | 16 | + | + | − | − | Yes | Yes |

Example 3

Several compositions that have been evaluated for viscosity as a function of temperature. The compositions are described below:

TABLE 2

Comparative Sample A

| Component | parts by weight (g) | % by weight | Physical Appearance at 23° C. | Physical Appearance at body temp |
|---|---|---|---|---|
| Urea hydrogen peroxide | 20 | 20 | Low viscosity, colorless liquid | Low viscosity, Colorless liquid |
| Water | 80 | 80 | | |

TABLE 3

Sample B

| Component | Parts by weight (g) | % by weight | Physical Appearance at 23° C. | Physical Appearance at Body temp |
|---|---|---|---|---|
| Urea hydrogen | 20 | 16 | Low viscosity, Colorless liquid | non-flowing, colorless gel |
| Water | 80 | 64 | | |
| PLURONIC F-127 | 25 | 20 | | |

TABLE 4

Sample C

| Component | Parts by weight (g) | % by weight | Physical Appearance at 23° C. | Physical Appearance at body temp |
|---|---|---|---|---|
| Urea hydrogen peroxide | 1.6 | 14.7 | Non-flowing, colorless gel | Non-flowing, colorless gel |
| Water | 6.4 | 58.7 | | |
| PLURONIC F-127 | 2.0 | 18.3 | | |
| CAB-O-SIL M-5* (fumed silica) | 0.9 | 8.3 | | |

*available from Cabot Corp. (Boston, MA)

Samples were further evaluated for viscosity as a function of temperature between 15° C. and 45° C. utilizing a Rheometrics RDA II Rheometer. Complex viscosity, $\eta^*$ (units of measure is in Poise), versus temperature data were obtained using a controlled strain rheometer ("RDA2", Rheometrics Scientific, Piscataway, N.J.). A parallel plate geometry was used with a plate diameter of 25 mm and a gap of approximately 1 mm. Samples were subjected to an oscillatory strain of 10% applied at a frequency of 1 rad/sec while the temperature was ramped from 15° C. and 45° C. (3° C./ min).

Set out below is the RDA viscosity data. FIG. 1 illustrates that aqueous compositions containing PLURONIC F127 polymer exhibit a relatively sharp increase in viscosity upon warming from room temperature to about 45° C. Sample C which exhibited semi-solid-like characteristics at room temperature (due to the incorporation of a filmed silica) also increased substantially upon an increase in temperature.

TABLE 5

| A | | B | | C | |
|---|---|---|---|---|---|
| Temp ° C. | $\eta^*$ P | Temp ° C. | $\eta^*$ P | Temp ° C. | $\eta^*$ P |
| 14.02 | 9.75424 | 17.88 | 2308.56 | 18.5 | 52951.5 |
| 14.28 | 3.35258 | 17.88 | 2379.72 | 18.3 | 42757.9 |
| 15.36 | 7.33292 | 18.54 | 2587.46 | 18.79 | 41559.9 |
| 17.28 | 3.46242 | 19.42 | 3111.41 | 19.64 | 41144.7 |
| 19.46 | 5.85152 | 20.91 | 3711.59 | 20.76 | 41347.4 |
| 21.12 | 5.79953 | 22.36 | 4580.71 | 22.09 | 42047 |
| 22.89 | 7.09599 | 23.72 | 5661.42 | 23.51 | 43615.7 |
| 24.91 | 4.19887 | 25.46 | 7221.65 | 24.04 | 45494.3 |
| 26.31 | 0.87001 | 26.85 | 8940.38 | 26.03 | 48768.7 |
| 28.23 | 3.13629 | 28.73 | 25375.6 | 27.94 | 55250.6 |
| 30.12 | 4.57411 | 30.7 | 29698.2 | 29.57 | 82062.6 |
| 31.6 | 4.7215 | 32.07 | 33651.8 | 31.31 | 94988.5 |
| 33.2 | 9.01765 | 33.57 | 37181.2 | 32.83 | 1.04E+05 |
| 35.02 | 8.0025 | 35.22 | 40557.8 | 34.36 | 1.09E+05 |
| 36.75 | 2.94618 | 36.89 | 43766.3 | 36.09 | 1.13E+05 |
| 38.44 | 4.24626 | 38.43 | 46677.4 | 37.49 | 1.20E+05 |
| 40.85 | 1.08273 | 40.01 | 49322.7 | 38.95 | 1.26E+05 |
| 42.92 | 5.04081 | 41.84 | 52296.6 | 40.7 | 1.32E+05 |
| | | 43.52 | 54490.4 | 42.2 | 1.36E+05 |
| | | | | 43.9 | 1.39E+05 |

We claim:

1. A method of whitening teeth in the oral environment using a dental composition comprising a tooth whitening agent and about 10% by weight to about 50% by weight of a thermally responsive viscosity modifier, wherein the composition is in a low viscosity liquid state at a pre-treatment temperature and a highly viscous state at a treatment temperature that is higher than the pre-treatment temperature, comprising:
    applying the composition through an orifice of a syringe onto a tooth surface, wherein the composition is at the pretreatment temperature and in the low viscosity liquid state prior to being applied onto the tooth surface,
    allowing the composition to warm to the treatment temperature and increase in viscosity to the highly viscous state wherein the viscosity of the composition at the treatment temperature is at least about 10 times the viscosity of the composition at the pre-treatment temperature, and
    allowing the composition to remain on the tooth surface for a sufficient time to effectuate whitening, whereby said high viscosity dental whitening composition if pre-gelled or pre-thickened being difficult to extrude through a small orifice, said free flowing low viscosity liquid dental whitening composition being readily deliverable through a syringe to target sites on the tooth surface intended to be whitened where it thickens and forms an immobile gel on the target site which is at or near about 30° C. to about 39° C. where it is kept for the desired period of time to effect whitening, said composition being readily removable from the tooth surface by cooling the material below the liquid to semi-solid transition temperature, and thereby reversing the thickening effect.

2. The method of claim 1 wherein the pre-treatment temperature is room temperature.

3. The method of claim 1 wherein the treatment temperature is body temperature.

4. The method of claim 1 wherein the thermally responsive viscosity modifier is a polyoxyalkylene polymer.

5. The method of claim 1 wherein the whitening agent is selected from the group consisting of hydrogen peroxide, carbamide peroxide, sodium hypochlorite, and mixtures thereof.

6. The method of claim 1 wherein the composition further comprises a solvent.

7. The method of claim 6 wherein the solvent comprises water.

8. The method of claim 1 wherein the visosity of the composition at the treatment temperature is about 10 times to about 100 times the viscosity of the composition at the pre-treatment temperature.

9. The method of claim 1 wherein the composition decreases in viscosity upon cooling from the treatment temperature.

10. The method of claim 9 further comprising removing the composition from the tooth surface by cooling the composition from the treatment temperature.

11. The method of claim 10 wherein the composition is cooled by application of a cool liquid.

12. The method of claim 11 wherein the liquid comprises water.

13. A method of whitening teeth in the oral environment using a dental composition comprising a tooth whitening agent and about 10% by weight to about 50% by weight of a thermally responsive viscosity modifier, wherein the composition is in a low viscosity semi-solid state at a pre-treatment temperature and a highly viscous state at a treatment temperature that is higher than the pre-treatment temperature, comprising:

applying the composition through an orifice of a syringe onto a surface, wherein the composition is at the pretreatment temperature and in the low viscosity semi-solid state prior to being applied onto the surface, allowing the composition to warm to the treatment temperature and increase in viscosity to the highly viscous state wherein the viscosity of the composition at the treatment temperature is at least about 2 times the viscosity of the composition at the pre-treatment temperature, and allowing the composition to remain on the tooth surface for a sufficient time to effectuate whitening, whereby said high viscosity dental whitening composition if pre-gelled or pre-thickened being difficult to extrude through a small orifice, said free flowing low viscosity semi-solid dental whitening composition being readily deliverable through a syringe to target sites on the the surface intended to be whitened where it thickens and forms an immobile gel on the target site which is at or near about 30° C. to about 39° C. where it is kept for the desired period of time to effect whitening, said composition being readily removable from the tooth surface by cooling the material below the low viscosity semi-solid to highly viscous solid transition temperature, and thereby reversing the thickening effect.

14. The method of claim 13 wherein the pre-treatment temperature is room temperature.

15. The method of claim 13 wherein the treatment temperature is body temperature.

16. The method of claim 13 wherein the viscosity of the composition at the treatment temperature is about 2 times to about 5 times the viscosity of the composition at the pre-treatment temperature.

17. The method of claim 13 wherein applying the composition onto a surface comprises applying the composition onto a tooth surface.

18. A method of whitening teeth in the oral environment using a dental composition comprising a tooth whitening agent and about 10% by weight to about 50% by weight of a thermally responsive viscosity modifier, wherein the composition is in a low viscosity semi-solid state at a pre-treatment temperature and a highly viscous state at a treatment temperature that is higher than the pre-treatment temperature, comprising:

applying the composition through an orifice of a syringe onto a surface, wherein the composition is at the pretreatment temperature and in the low viscosity semi-solid state prior to being applied onto the surface, allowing the composition to warm to the treatment temperature and increase in viscosity to the highly viscous state wherein the viscosity of the composition at the treatment temperature is at least about 10 times the viscosity of the composition at the pre-treatment temperature, and allowing the composition to remain on the surface for a sufficient time to effectuate whitening.

19. The method of claim 18 wherein applying the composition onto a surface comprises applying the composition onto a tooth surface.

20. The method of claim 18 wherein applying the composition through an orifice comprises applying the composition through an orifice of a syringe.

* * * * *

UNITED STATES PATENT AND TRADEMARK OFFICE
CERTIFICATE OF CORRECTION

PATENT NO. : 6,312,666 B1  
DATED : November 6, 2001  
INVENTOR(S) : Joel D. Oxman and Matt C. Trom It is certified that error appears in the above-identified patent and that said Letters Patent is hereby corrected as shown below:

Column 4,  
Line 53, please delete the word "copolymer" and insert in place thereof -- copolymers --.  
Line 64, please delete "$(c_2H_4O)$" and insert in place thereof -- $(C_2H_4O)$ --.

Column 8,  
Line 2, please insert a space between the words "evaluated" and "for".

Column 11,  
Line 5, please delete the word "visosity" and insert in place thereof -- viscosity --.

Signed and Sealed this

Twenty-eighth Day of January, 2003

JAMES E. ROGAN  
*Director of the United States Patent and Trademark Office*